(12) United States Patent
Dittes (10) Patent No.: US 9,995,344 B2
(45) Date of Patent: Jun. 12, 2018

(54) CAPACITANCE MEASUREMENT IN A BEARING

(71) Applicant: AKTIEBOLAGET SKF, Göteborg (SE)

(72) Inventor: Nicholas Dittes, Sjulsmark (SE)

(73) Assignee: AKTIEBOLAGET SKF, Gothenburg (SE)

( * ) Notice: Subject to any disclaimer, the term of this patent is extended or adjusted under 35 U.S.C. 154(b) by 0 days. days.

(21) Appl. No.: 15/308,710

(22) PCT Filed: May 13, 2015

(86) PCT No.: PCT/SE2015/050544
§ 371 (c)(1),
(2) Date: Nov. 3, 2016

(87) PCT Pub. No.: WO2015/178826
PCT Pub. Date: Nov. 26, 2015

(65) Prior Publication Data
US 2017/0159716 A1    Jun. 8, 2017

(30) Foreign Application Priority Data
May 19, 2014   (SE) ...................................... 1450586

(51) Int. Cl.
*F16C 41/00*  (2006.01)
*G01N 33/28*  (2006.01)
(Continued)

(52) U.S. Cl.
CPC .......... *F16C 41/002* (2013.01); *F16C 19/525* (2013.01); *F16C 33/6688* (2013.01); *F16J 15/324* (2013.01); *G01M 13/04* (2013.01); *G01N 27/223* (2013.01); *G01N 33/2847* (2013.01); *G01N 33/2888* (2013.01); *F16C 2233/00* (2013.01); *F16C 2360/31* (2013.01)

(58) Field of Classification Search
CPC .. F16C 19/525; F16C 41/002; F16C 33/6688; F16C 2233/00; F16C 2360/31;
(Continued)

(56) References Cited

U.S. PATENT DOCUMENTS 3,564,477 A * 2/1971 Pompei ............... F16C 33/7843
                                                439/17
4,898,480 A * 2/1990 Raj ..................... F16C 33/6644
                                                277/410
(Continued)

FOREIGN PATENT DOCUMENTS

EP    0288940 A2    4/1988
EP    2667491 A1 * 11/2013  ............. H02K 1/276
(Continued)

*Primary Examiner* — Marcus Charles
(74) *Attorney, Agent, or Firm* — Bryan Peckjian; SKF USA Inc. Patent Dept.

(57) ABSTRACT

A bearing arrangement includes a bearing having an inner race and an outer race and a plurality of rolling elements arranged between the inner and outer race such that the first race is rotatable relative the second race; bearing lubricant arranged within the bearing to lubricate the rolling elements. The bearing arrangement provides a first electrically conductive portion and a second electrically conductive portion, the first and second electrically conductive portion being electrically insulated and arranged such that at least a portion of the bearing lubricant is located between the first and second electrically conductive portion; and a capacitance meter having a first electrode connected to the first electrically conductive portion and a second electrode connected to the second electrically conductive portion, configured to measure a capacitance between the first ring and the second ring to determine a water content in the lubricant based on the measured capacitance.

13 Claims, 4 Drawing Sheets

(51) Int. Cl.
*G01M 13/04* (2006.01)
*G01N 27/22* (2006.01)
*F16C 19/52* (2006.01)
*F16C 33/66* (2006.01)
*F16J 15/32* (2016.01)
*F16J 15/324* (2016.01)

(58) Field of Classification Search
CPC .............. G01M 13/04; G01N 33/2847; G01N 32/2888; G01N 2233/00; F16N 9/02; F16J 15/162; F16J 15/324
USPC .... 384/448, 462, 474, 476–478, 493; 73/10, 73/53.05, 54.02; 422/82.02, 82.12
See application file for complete search history.

(56) References Cited

U.S. PATENT DOCUMENTS

| | | | | |
|---|---|---|---|---|
| 6,324,899 | B1* | 12/2001 | Discenzo | F16C 19/52 340/631 |
| 2009/0285512 | A1* | 11/2009 | Gebert | F16C 33/32 384/44 |
| 2009/0304318 | A1* | 12/2009 | Konno | F16C 19/52 384/492 |
| 2011/0116733 | A1* | 5/2011 | Siraky | F16C 41/00 384/448 |
| 2011/0206306 | A1* | 8/2011 | Urano | F16J 15/162 384/473 |
| 2011/0317953 | A1* | 12/2011 | Moratz | F16C 33/7843 384/572 |
| 2013/0293036 | A1* | 11/2013 | Yamamoto | H02K 1/276 310/43 |

FOREIGN PATENT DOCUMENTS

| | | | | |
|---|---|---|---|---|
| EP | 2682732 A1 | | 1/2014 | |
| JP | 05126141 A | * | 5/1993 | ............. F16C 23/04 |
| JP | 2004308742 A | * | 11/2004 | ............. F16C 19/24 |
| JP | 2007057076 A | * | 3/2007 | ............. F16C 33/46 |
| JP | 2007198576 A | | 8/2007 | |
| JP | 2013050193 A | * | 3/2013 | ............. F16C 33/66 |
| WO | 03054482 A2 | | 7/2003 | |
| WO | WO-2008099562 A1 | * | 8/2008 | ............. F16C 19/52 |

\* cited by examiner

CAPACITANCE MEASUREMENT IN A BEARING

CROSS REFERENCE

This is a United States National Stage Application claiming the benefit of International Application Number PCT/SE2015/050544 filed on May 13, 2015, which claims the benefit of Swedish Patent Application 1450586-1 filed on May 19, 2014, both of which are incorporated herein by reference in their entireties.

FIELD OF THE INVENTION

The present invention relates to a bearing arrangement. In particular, the present invention relates to a bearing comprising a capacitance sensor for determining a characteristic of a lubricant in the bearing.

BACKGROUND OF THE INVENTION

Bearings and in particular rolling bearings are used in a wide range of applications comprising rotating shafts. Rolling bearings provide low friction rotation by means of the rolling elements arranged between the outer and inner race of the bearing. To further reduce the friction between the rolling elements and the races, thereby increasing the life length of the bearing, a bearing lubricant such as grease or oil is often used to lubricate the rolling elements.

In order to improve the availability/up-time and life span of, for example, a wind turbine, various bearing related parameters may be monitored, such as, vibrations, lubricant pressure, lubricant quality, lubricant temperature and bearing load.

It has been found that bearing failures are often caused by water in the bearing lubricant. Water in the lubricant can cause surface erosion and cavitations within the bearing. Also, it can cause hydrogen embrittlement due to the extreme pressures in rolling element bearings, which can be as high as 1 to 3 GPa, where water can break down into its constituent atoms causing hydrogen to penetrate the surface of the bearing elements and cause the surface to become more brittle. Water can also cause additives to precipitate and cause abrasive particles or sludge to form. Water also causes the base oil to oxidize much more quickly. Even without the addition of external water, water content in the lubricant may increase slightly due to oxidation of hydrocarbons in the lubricant.

For example, a bearing exposed to the elements (such as a wheel bearing on a train or car) is more susceptible to contamination, both by water and by other contaminating particles.

Accordingly, it is important to be able to monitor the condition of the bearing so that a bearing can be replaced before it breaks.

Although the monitoring that is currently described in the art helps the scheduling of maintenance and prediction of failures before they occur, and thereby may improve the availability of rotating systems, many such systems are both complicated and impractical to use in many applications.

BRIEF SUMMARY OF THE INVENTION

In view of the above-mentioned desired properties of a bearing, and the above-mentioned and other drawbacks of the prior art, it is an object of the present invention to provide an improved bearing and a method for monitoring the properties of the bearing so that unexpected bearing failure may be avoided.

According to a first aspect of the present invention, it is therefore provided a bearing arrangement comprising: a bearing having an inner race, an outer race and a plurality of rolling elements arranged between the inner and outer race such that the first race is rotatable relative the second race; bearing lubricant arranged within the bearing to lubricate the rolling elements; wherein the bearing arrangement provides a first electrically conductive portion and a second electrically conductive portion, the first and second electrically conductive portion being electrically insulated and arranged such that at least a portion of the bearing lubricant is located between the first and second electrically conductive portion; and a capacitance meter having a first electrode connected to the first electrically conductive portion and a second electrode connected to the second electrically conductive portion, configured to measure a capacitance between the first portion and the second portion to determine a water content in the lubricant based on the measured capacitance.

As the capacitance of the lubricant depends on the composition of the lubricant, any change in composition resulting in different dielectric properties of the lubricant would lead to a change in capacitance. In particular, the dielectric constant of water is considerably higher than the dielectric constant of conventionally used bearing lubricants such as bearing grease and oil. Thus, the addition of water to the bearing lubricant would lead to an increase in the observed capacitance. Through early detection of water in the bearing lubricant, the occurrence of bearing failures can be significantly reduced. It is also possible to detect the presence of other contaminants in the lubricant, such as metallic particles, which also leads to a change in capacitance. Capacitance measurements are well known and the above described invention may easily be incorporated in new bearings, and capacitance measurement equipment may also be retrofit in existing bearings.

Capacitance is measured between two conducting elements which are separated by a dielectric material. The conducting elements are electrically insulated, meaning that they are not electrically connected to each other or to any other part of the bearing, they are only connected to the respective electrode of the capacitance meter. In the present application, the dielectric material is the bearing lubricant and the conducting portions may be parts of the bearing or separately provided conducting elements. Non-conductive greases and oils commonly used in bearings have a dielectric constant of about 2-5, whereas water has a dielectric constant of about 80 at room temperature. Thus, even a small amount of water in the lubricant would lead to a change in capacitance due to the large difference in dielectric constant, which makes it possible to detect a small content of water.

During normal operation of a bearing, no significant change in capacitance is expected. Thus, any change in capacitance during operation can be regarded as an indication that something is wrong. A sudden increase in capacitance can indicate the addition of water or contaminants. A sudden decrease could indicate physical damage to the bearing, such as a damaged seal where the grease suddenly flows out. Furthermore, the capacitance may be measured both during operation, i.e. when the bearing is rotating, and when the bearing is still.

In one embodiment of the invention, the first electrically conductive portion and the second electrically conductive portion may be a first and a second sealing ring arranged on respective sides of the bearing, each sealing ring being electrically insulated from the bearing. Sealing rings are often present in a bearing to contain the lubricant within the bearing. By using electrically conducting sealing rings, the sealing rings may be used to measure the capacitance of the bearing lubricant. The sealing rings then act as the plates in a parallel plate capacitor. The sealing rings are electrically insulated from the bearing so as to not form a short circuit.

In one embodiment of the invention, the first electrically conductive portion may be a perforated ring concentrically arranged between the inner race and the outer race within the bearing. The use of a perforated ring makes it possible to position the ring within the bearing, where the perforations in the ring allow lubricant to flow through the ring. The perforations may also be referred to as openings or holes. When a perforated ring arranged within the bearing is used, the capacitance may for example be measured between the perforated ring and either one of sealing rings arranged on the sides of the bearing. By separately measuring the capacitance between the perforated ring and each of the sealing rings, it may be possible to detect if the properties of lubricant is different on the respective sides on the perforated ring. This may for example be advantageous as it may be possible to detect from which side of the bearing water is entering into the bearing.

Moreover, the in the case of a perforated ring arranged within the bearing, the capacitance may also be measured between the perforated ring and either of the inner or the outer race.

According to one embodiment of the invention, the bearing arrangement according may further provide an electrically insulating frame arranged between the sealing ring and the bearing to electrically insulate the sealing ring from the bearing. A typically ring-shaped frame may be used to electrically insulate the sealing ring from the bearing. The frame may for example be made from a plastic or rubber material.

In one embodiment of the invention, the bearing arrangement may further provide a bearing housing in which the bearing is arranged, wherein the first electrically conductive portion and the second electrically conductive portion is a first and a second perforated ring arranged on respective sides of the bearing, each perforated ring being electrically insulated from the bearing. The bearing may be arranged in a bearing housing, and the lubricant is arranged within the housing which is sealed so that the lubricant does not escape the bearing housing. The perforated rings arranged on the sides of the bearing allow the lubricant to flow through the rings between the housing and the inside of the bearing.

In one embodiment of the invention, the bearing arrangement may further provide a temperature sensor configured to determine the temperature of the lubricant. The temperature of the lubricant may vary significantly during operation of the bearing, and there may in particular be a difference in temperature when comparing a static bearing with a bearing rotating at high speed. In general, the dielectric constant of lubricant and oil does not vary significantly with temperature. On the other hand, the dielectric constant of water varies greatly with temperature. Thereby, by measuring the temperature, a small change in capacitance which may be interpreted as small change in water content of the lubricant, may instead be correctly attributed to a varying temperature. Moreover, by observing the temperature dependent capacitance, the actual water content in the lubricant may be more accurately determined. The temperature sensor may be any type of temperature sensor known by the skilled person.

In one embodiment of the invention, the capacitance meter is configured to measure the capacitance at various frequencies or over a sine sweep. Frequency here refers to the frequency of an alternating current used by the capacitance meter to measure the capacitance. Grease has a different frequency dependence on the dielectric constant than water, and water has a well-known dielectric constant (relative permittivity) that varies with frequency. Hence, the frequency dependence can be taken advantage of in order to estimate water content. Measuring the capacitance at various frequencies or over a sine sweep allows for estimation of water content even if the grease content is changing or the location of the grease is changing in the bearing.

According to a second aspect of the invention, there is also provided a method for determining a condition of a lubricant in a bearing comprising: a bearing having an inner race, an outer race and a plurality of rolling elements arranged between the inner and outer race such that the first race is rotatable relative the second race; a bearing lubricant arranged within the bearing to lubricate the rolling elements; and a first electrically conductive portion and a second electrically conductive portion, the first and second electrically conductive portion being electrically insulated from each other and arranged such that at least a portion of the bearing lubricant is located between the first and second electrically conductive portion; the method comprising: measuring a value indicative of a capacitance between the first electrically conductive portion and the second electrically conductive portion; determining a difference between the measured value and a predetermined value; and if the difference is larger than a first predetermined threshold value, determine that properties of the lubricant have changed.

The measured value indicative of the capacitance between the first and second electrically conductive portion may for example be the capacitance measured directly at a predetermined frequency, or a ratio of capacitances measured at two different frequencies, or the temperature derivative of the capacitance, $dC/dT$.

In one embodiment of the invention, the predetermined value with which the measured value is compared may be a previously measured value for the same bearing in the same application. Alternatively, or in combination, the measured value may also be compared with a reference value based on measurements on a similar bearing. The reference value may also be based on analytical models and simulations.

If a detected difference is smaller than a predetermined threshold value, it may be determined that the difference is only the result of noise or within the range of known measurement uncertainties. Moreover, the threshold value may also be used to avoid that the temperature dependence of the dielectric constant of the lubricant is mistakenly identified as a change in water content of the lubricant. In particular, where it is known that the change in capacitance due to change in temperature of the lubricant is within a certain range, only detected capacitances outside of that known range is taken to represent a change in composition of the lubricant.

Moreover, by observing the temperature dependence of the capacitance, it may be possible to accurately determine the actual water content of the lubricant by correlating the observed temperature dependence with the known temperature dependence of water for different percentages of water in the lubricant.

Furthermore, if the water content in the lubricant has been accurately determined, for example by a direct capacitance measurement or by observing the temperature derivative, the total amount of lubricant present in the bearing can be approximated. Since the dielectric constants of water and grease are generally known and the remainder of the system should be constant, this can be accomplished. This eliminates the scenario where a loss in grease plus a slight addition of water would represent a similar capacitance of a properly lubricated bearing with the correct amount of grease and no water since the water introduces a temperature dependence to the dielectric constant.

Further effects and features of this second aspect of the present invention are largely analogous to those described above in connection with the first aspect of the invention.

Moreover, further features of, and advantages with, the present invention will become apparent when studying the appended claims and the following description. The skilled person realize that different features of the present invention may be combined to create embodiments other than those described in the following, without departing from the scope of the present invention.

BRIEF DESCRIPTION OF THE SEVERAL VIEWS OF THE DRAWING

These and other aspects of the present invention will now be described in more detail with reference to the appended drawings showing an example embodiment of the invention, wherein.

DETAILED DESCRIPTION OF THE INVENTION

In the present detailed description, various embodiments of bearing arrangement according to the present invention are mainly discussed with reference to a ball bearing. It should be noted that this by no means limits the scope of the present invention which is equally applicable to any type of bearing comprising a lubricant.

Figure 1:
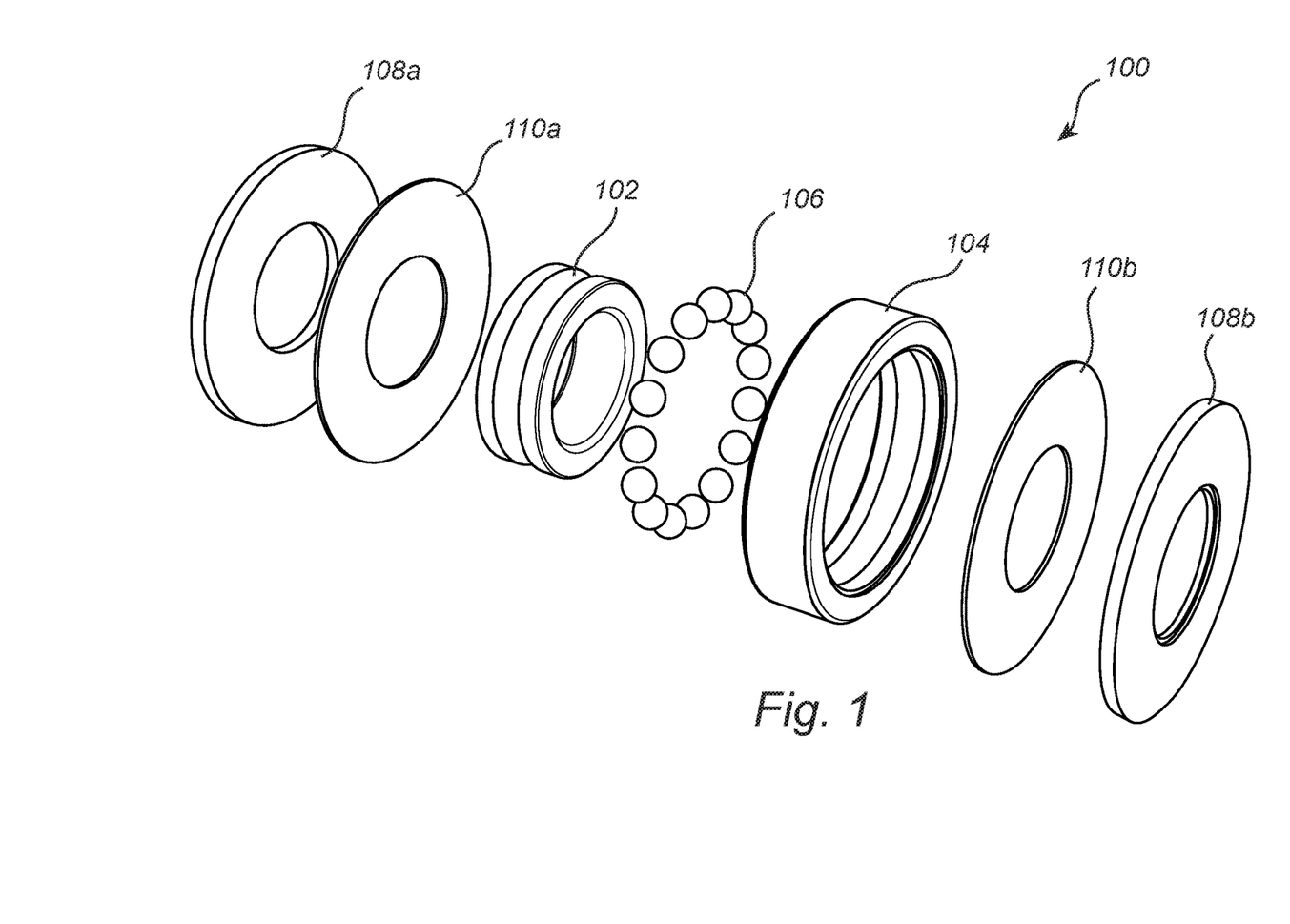
FIG. 1 schematically illustrates an exploded view of a bearing arrangement according to an embodiment of the invention.

FIG. 1 is an exploded view of a bearing 100 comprising an inner race 102, an outer race 104 and a plurality of rolling elements 106 in the form of balls arranged between the inner and outer race. The bearing further provides sealing rings 108a-b arranged on the respective sides of the bearing to seal the bearing. Herein, both the sealing rings 108a-b and the races 102,104 are made from a conductive material. Furthermore, electrically insulating frames 110a-b are arranged to electrically insulate the sealing rings 108a-b from the races 102,104. A lubricant (not shown) is arranged within the bearing to provide lubrication for the rolling elements 106. Bearings are also commonly provided with a cage for keeping the rolling elements in place. Such cages may be arranged and configured in many different ways known by the skilled person, and bearing cages are therefore not shown herein to avoid complicating the drawings.

In FIG. 1, the first conductive portion is the first sealing ring 108a and the second conductive portion is the second sealing ring 108b, thereby forming a parallel plate capacitor where the lubricant acts as dielectric. Thus, by connecting a capacitance meter to the two sealing rings 108a-b, the capacitance of the lubricant can be measured.

Figure 2:
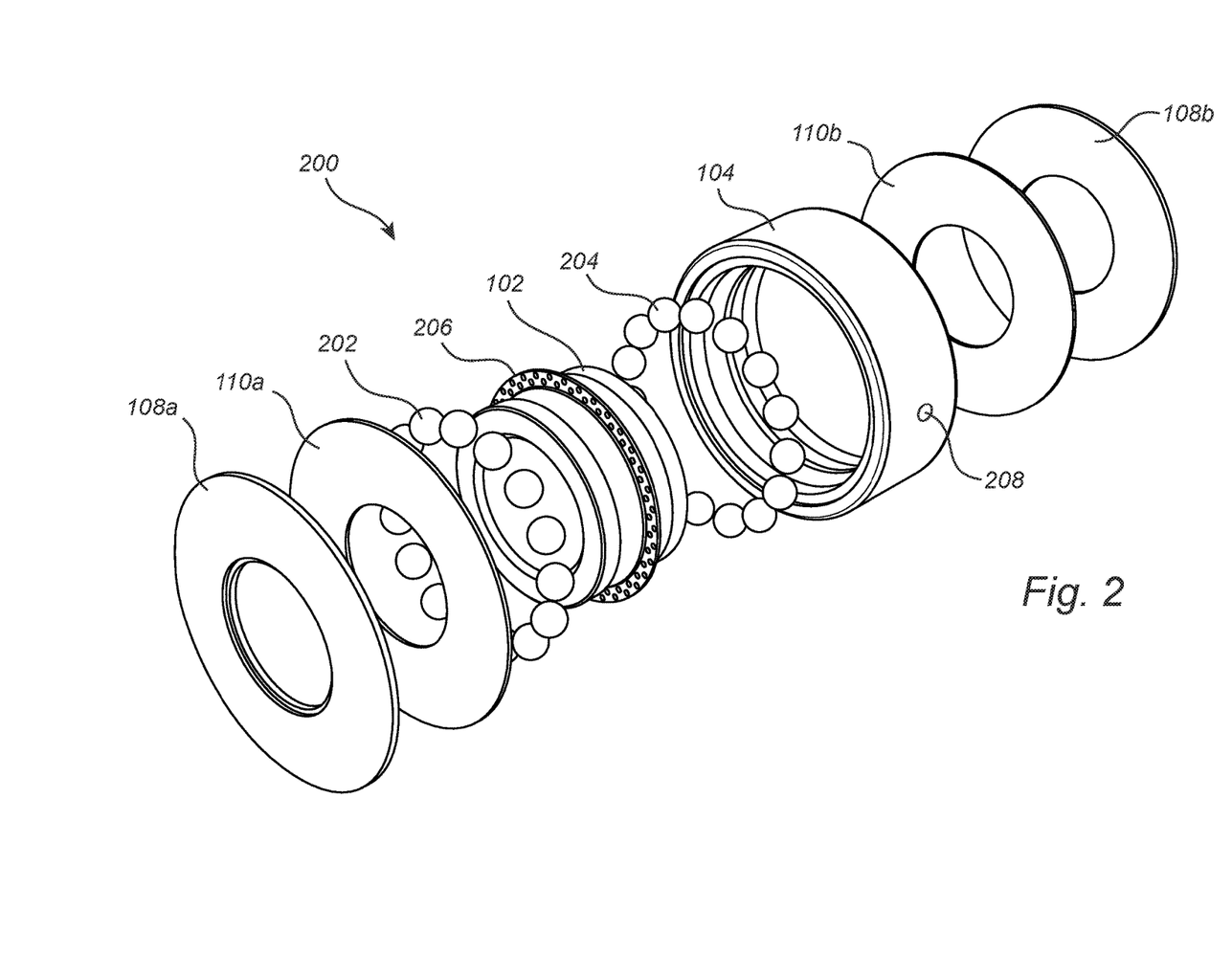
FIG. 2 schematically illustrates an exploded view of a bearing arrangement according to an embodiment of the invention.

In FIG. 2, a bearing 200 similar to the one illustrated in FIG. 1 is shown. The bearing in FIG. 2 provides two sets of rolling elements 202, 204, and a perforated plate 206 is arranged between the rows of rolling elements 202, 204. The perforated plate 206 is conductive and may be connected to one electrode of a capacitance meter. The connection may for example be made through an opening 208 in the outer race 104. Such an opening is preferably sealed with a sealing material to ensure that no lubricant escapes the bearing, and that no contaminants may enter into the bearing. It is of course also possible to form the connection through the inner race 102 or though either sealing ring 108a-b, depending on how a particular bearing is configured and on how it is arranged when in use. The perforation of the ring 206 allows the lubricant to move around within the bearing through the openings in the ring. By connecting a first electrode of a capacitance meter to the perforated ring 206, and by connecting the other electrode to either of the sealing rings 108a-b, the capacitance at either side of the perforated ring 206 can be measured. Thereby, it is not only possible to determine properties of the lubricant, it is also possible to detect if the properties of the lubricant are different for the respective sides of the bearing. This may for example be advantageous for identifying if a contaminant or water is entering into the bearing from either side of the bearing.

Figure 3:
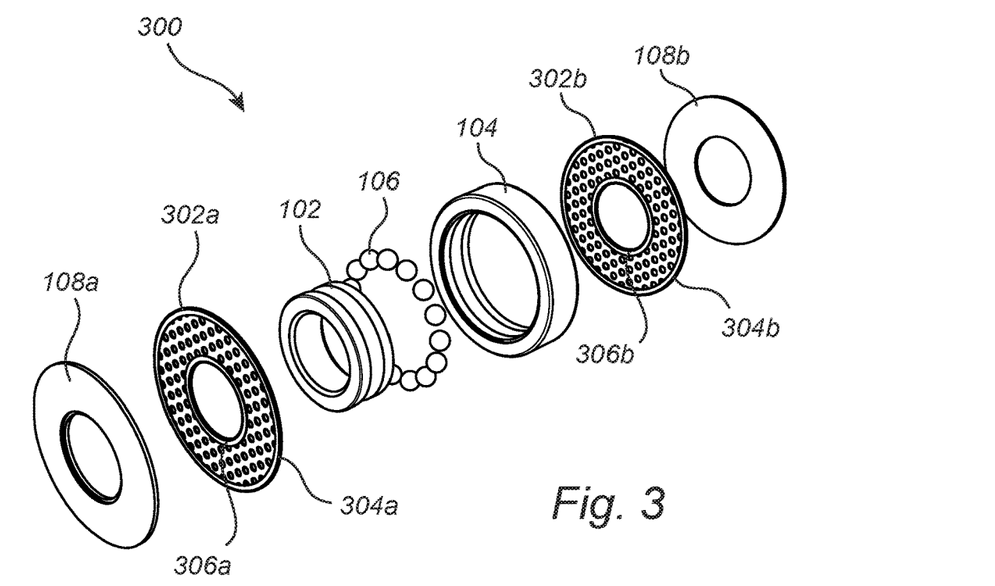
FIG. 3 schematically illustrates an exploded view of a bearing arrangement according to an embodiment of the invention.

FIG. 3 is a schematic illustration of a bearing 300 where perforated plates 302a-b are arranged between the respective sealing rings 108a-b and the bearing. Each of the perforated plates 302a-b provides a respective rim 304a-b, 306a-b arranged around both the inner and outer circumference of the plates 302a-b. The rims 304a-b, 306a-b, are preferable electrically insulating such that the plate is electrically insulated from the sealing rings and from the races. Moreover, the rims 304a-b, 306a-b may act as a distance such that a gap a formed between the perforated plates 302a-b and the corresponding sealing rings such that a lubricant may flow freely through the perforations.

Figure 4:
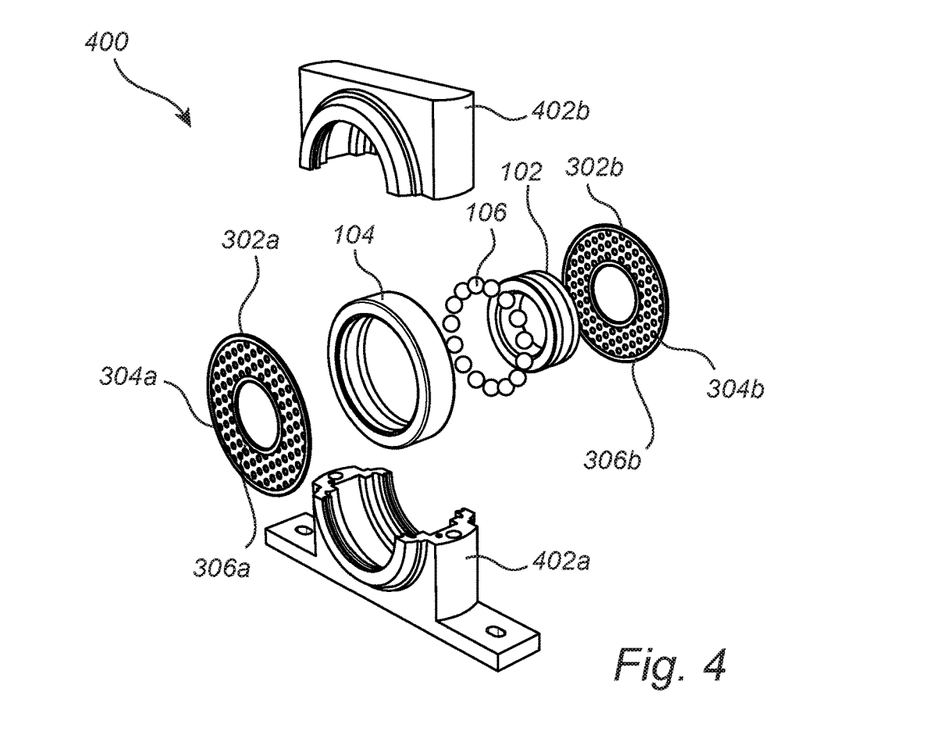
FIG. 4 schematically illustrates a bearing arrangement and a bearing housing according to an embodiment of the invention.

FIG. 4 is a schematic illustration of a bearing arrangement arranged in a bearing housing 402a-b. When the bearing is arranged in a housing, the housing acts to seal the bearing from the environment and no sealing rings are required. The perforated plates 302a-b may thus be arranged on the sides of the bearing without an additional sealing ring, and the bearing lubricant may then flow though the perforated rings 302a-b between the bearing housing and the inside of the bearing, such that the rolling elements 106 are lubricated.

Figure 5:
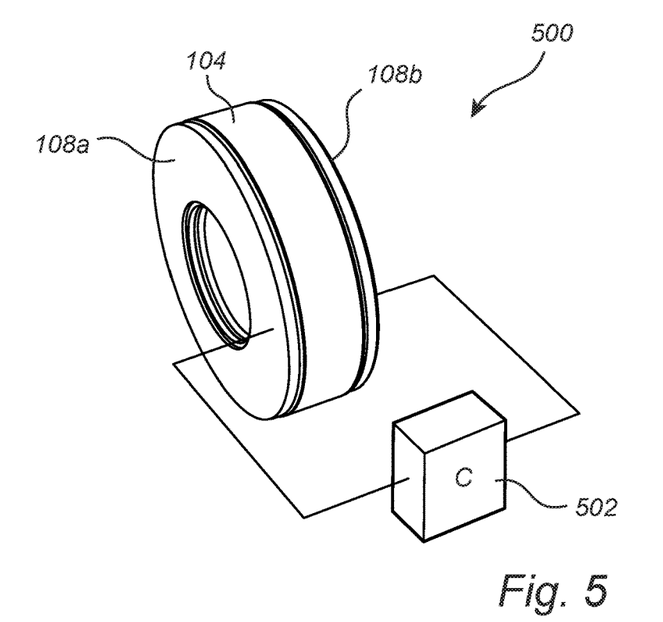
FIG. 5 schematically illustrates a bearing arrangement according to an embodiment of the invention.

FIG. 5 is a schematic illustration of a bearing arrangement 500 where a capacitance meter 502 is connected to each of the sealing rings 108a-b such that the capacitance between the plates can be measured. In some embodiments, the bearing arrangement also provides a temperature sensor (not shown) for determining the temperature of the grease. The temperature sensor may be arranged within the bearing, for example attached to a sealing ring or attached to or integrated in a cage. The temperature sensor may also be attached to the outside of the bearing as long as the relative influence of the measured temperature on the capacitance measurement is known.

Figure 6:
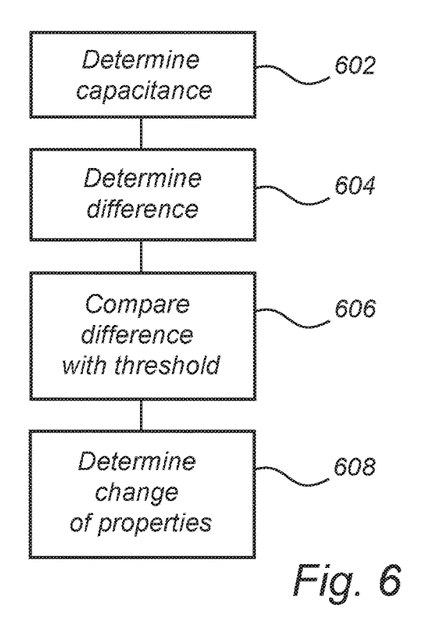
FIG. 6 is a flow chart outlining the general steps of a method according to an embodiment of the invention.

FIG. 6 is a flow chart outlining the general steps of a method according to an embodiment of the invention. First, 602, a capacitance measure is performed to determine a capacitance value. Next, 604, the measurement is compared to a predetermined value. The predetermined value may be a value based on previous measurements on a similar device, or it may be based on theoretical calculations. However, more preferably the predetermined value is a previously measured capacitance or the same bearing under similar conditions. It may for example be the most recently measured value prior to the current measurement. By continuously observing the capacitance to determine if there is a change in capacitance, changing properties of the bearing can be identified without knowing the specific capacitance of a bearing in a particular application.

The detected difference is also compared 506 with a threshold value, and the difference should also be larger than the threshold value to rule out variations caused for example by measurement inaccuracies. The threshold value can be set by performing calibration measurements. If the detected difference is larger than the threshold value, it is determined 508 that the properties of the lubricant have changed.

Typically, any increase in capacitance is a sign that the properties of the lubricant has changed in a way that is detrimental to the performance of the lubricant.

Moreover, the temperature derivative of the capacitance may be determined. The temperature derivative of the capacitance may for example be determined at a stage where the temperature of the lubricant is known to change, for example during startup or shut down of a rotating machine. The capacitance (or dielectric constant) may for example be measured twice at different temperatures of the bearing (such as when the machine first starts and when it is at operating temperature). Then, the temperature derivative can be compared to a known derivative to determine if the properties of the lubricant have changed. Furthermore, the temperature derivative of commonly used lubricants is typically close to zero, at least within the operating temperatures of a bearing. Accordingly, any non-zero temperature derivative may be taken as an indication that properties f the lubricant has changed. Water in particular has a temperature dependent dielectric constant making it possible to detect an addition of water as a change in temperature derivative of the lubricant.

Moreover, the capacitance (or dielectric constant) may be measured over various frequencies or over a sine sweep. Grease has a different frequency dependence on the dielectric constant than water, and water has a well known dielectric constant (relative permittivity) that varies with frequency. Hence, the frequency dependence can be taken advantage of in order to estimate water content. For example, a ratio of capacitance at two frequencies can be useful in representing water content. 90 Hz and 100 kHz may for example be used, wherein 90 Hz is beneficial since it is not a multiple of 50 or 60 Hz. Then, the ratio can be compared to a known or predetermined ratio to determine if the properties of the lubricant have changed.

In one scenario, the high frequency (e.g. 100 kHz) capacitance goes down significantly over time (or between two or more measurements). But at the same time, the low frequency (e.g. 90 Hz) capacitance is much higher than the high frequency measurement. This could be that some grease was lost (e.g. through a damaged seal) and water got inside the bearing. In another scenario, the high frequency capacitance only goes up a little bit, but the low frequency capacitance goes up significantly. This could be that the grease content has stayed roughly the same, but there has been water contamination. In yet another scenario, the high frequency capacitance measurement goes down by approximately the same percent as the low frequency measurement. This could mean that there has been no water contamination, but there has been some grease loss (or the grease moved significantly).

Even though the invention has been described with reference to specific exemplifying embodiments thereof, many different alterations, modifications and the like will become apparent for those skilled in the art. For example, the described invention may be used in many different types of bearings. Also, it should be noted that parts of the system may be omitted, interchanged or arranged in various ways, the bearing arrangement yet being able to perform the functionality of the present invention.

Additionally, variations to the disclosed embodiments can be understood and effected by the skilled person in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage.

The invention claimed is:

1. A bearing arrangement comprising:
    a bearing having an inner race, an outer race, and a plurality of rolling elements arranged between the inner and outer race such that a first race is rotatable relative a second race;
    a bearing lubricant arranged within the bearing to lubricate the rolling elements;
    a first electrically conductive portion and a second electrically conductive portion, the first and second electrically conductive portion being electrically insulated and arranged such that at least a portion of the bearing lubricant is located between the first and second electrically conductive portion; and
    a capacitance meter having a first electrode connected to the first electrically conductive portion and a second electrode connected to the second electrically conductive portion, configured to measure a capacitance between the first and second portion to determine a water content in the lubricant based on the measured capacitance,
    wherein the first electrically conductive portion and the second electrically conductive portion is a first and a second sealing ring arranged on respective sides of the bearing, each sealing ring being electrically insulated from the bearing; and
    an electrically insulating frame arranged between the sealing ring and the bearing to electrically insulate the sealing ring from the bearing.

2. The bearing arrangement according to claim 1, further comprising a bearing housing in which the bearing is arranged, wherein the first electrically conductive portion and the second electrically conductive portion is a first and a second perforated ring arranged on respective sides of the bearing, each perforated ring being electrically insulated from the bearing.

3. The bearing arrangement according to claim 1, further comprising a temperature sensor configured to determine the temperature of the lubricant.

4. The bearing arrangement according to claim 1, wherein the capacitance meter is configured to measure the capacitance at various frequencies or over a sine sweep.

5. A bearing arrangement comprising:
a bearing having an inner race, an outer race, and a plurality of rolling elements arranged between the inner and outer race such that a first race is rotatable relative a second race;
a bearing lubricant arranged within the bearing to lubricate the rolling elements;
a first electrically conductive portion and a second electrically conductive portion, the first and second electrically conductive portion being electrically insulated and arranged such that at least a portion of the bearing lubricant is located between the first and second electrically conductive portion; and
a capacitance meter having a first electrode connected to the first electrically conductive portion and a second electrode connected to the second electrically conductive portion, configured to measure a capacitance between the first and second portion to determine a water content in the lubricant based on the measured capacitance,
wherein the first electrically conductive portion is a perforated ring concentrically arranged between the inner race and the outer race within the bearing,
wherein the second electrically conductive portion is a sealing ring arranged on a side of the bearing and electrically insulated from the bearing,
wherein the second electrically conductive portion is the inner or outer race of the bearing.

6. A method for determining a condition of a lubricant in a bearing comprising:
providing a housing having an inner race and an outer race; a plurality of rolling elements arranged between the inner and outer race such that a first race is rotatable relative a second race; a bearing lubricant arranged within the housing to lubricate the rolling elements; and a first electrically conductive portion and a second electrically conductive portion, the first and second electrically conductive portion being electrically insulated from each other and arranged such that at least a portion of the bearing lubricant is located between the first and second electrically conductive portion; the method comprising:
measuring a value indicative of a capacitance between the first electrically conductive portion and the second electrically conductive portion;
determining a difference between the measured value and a predetermined value; and
if the difference is larger than a first predetermined threshold value, determine that properties of the lubricant have changed,
wherein the first electrically conductive portion and the second electrically conductive portion is a first and a second sealing ring arranged on respective sides of the bearing, each sealing ring being electrically insulated from the bearing; and
wherein an electrically insulating frame is arranged between the sealing ring and the bearing to electrically insulate the sealing ring from the bearing.

7. The method according to claim 6, wherein the step of measuring comprises measuring the capacitance.

8. The method according to claim 6, further comprising measuring the temperature of the lubricant.

9. The method according to claim 8, wherein the step of measuring comprises measuring the temperature derivative of the capacitance, dC/dT.

10. The method according to claim 9, wherein the predetermined value is a previously measured value for the same bearing.

11. The method according to claim 10, wherein if the measured value is larger than the predetermined value, it is determined that the water content of the lubricant is increased.

12. The method according to claim 9, further comprising continuously monitoring the capacitance during operation of the bearing in a rotating machine.

13. The method according to claim 6, wherein the step of measuring comprises measuring the capacitance at two or more different frequencies.

* * * * *